United States Patent [19]

Hopkins

[11] 3,968,788

[45] July 13, 1976

[54] SPHYGOMANOMETER BAND AND METHOD OF SELF-APPLICATION THEREOF

[76] Inventor: John Paxton Hopkins, 4146 Blvd. Place, Mercer Island, Wash. 98040

[22] Filed: May 29, 1975

[21] Appl. No.: 581,715

[52] U.S. Cl............................ 128/2.05 C; 128/327; 128/DIG. 3
[51] Int. Cl.² ............................................ A61B 1/00
[58] Field of Search............. 128/2.05 C, 2.06, 327, 128/DIG. 3

[56] References Cited
UNITED STATES PATENTS

| | | | |
|---|---|---|---|
| 1,063,287 | 6/1913 | Rogers et al.................... | 128/2.05 G |
| 2,029,912 | 2/1936 | Cossor............................. | 128/327 |
| 2,444,161 | 6/1948 | Hanafin ............................. | 128/327 |
| 2,582,123 | 1/1952 | Heitz................................ | 128/327 X |
| 3,051,179 | 8/1962 | Dwyer.............................. | 128/327 |
| 3,606,880 | 9/1971 | Ogle................................. | 128/2.05 C |
| 3,713,446 | 1/1973 | Sarnoff............................. | 128/327 |

Primary Examiner—Delbert B. Lowe
Attorney, Agent, or Firm—Christensen, O'Connor, Garrison & Havelka

[57] ABSTRACT

The pliant, elongate inflatable band of a sphygomanometer is provided with a pair of elongate tensioning cords each extending from one end of the band to assist a patient in applying the band to an upper portion of his arm without the assistance of another person, thus allowing the patient to take his own blood pressure measurement.

6 Claims, 5 Drawing Figures

U.S. Patent  July 13, 1976  3,968,788
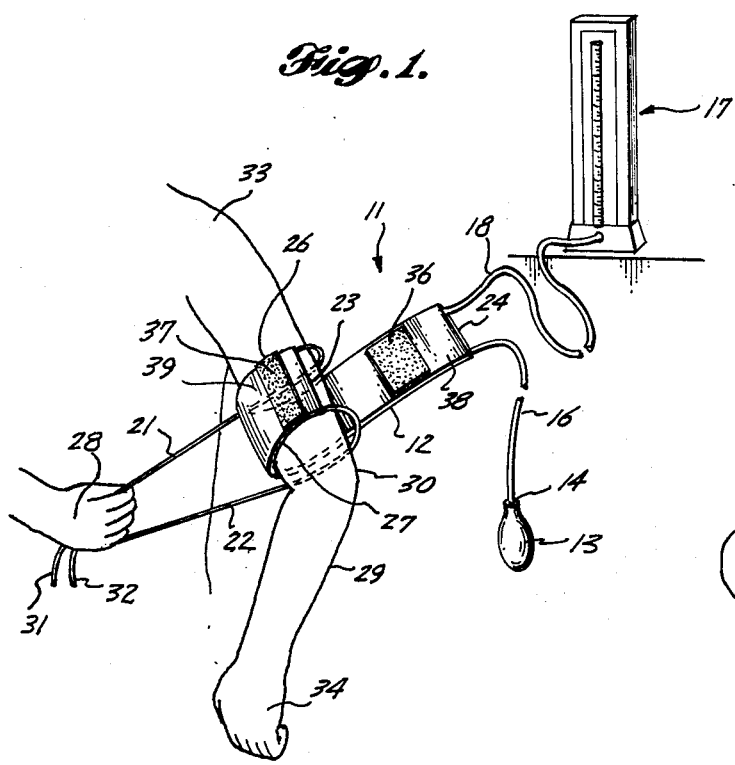
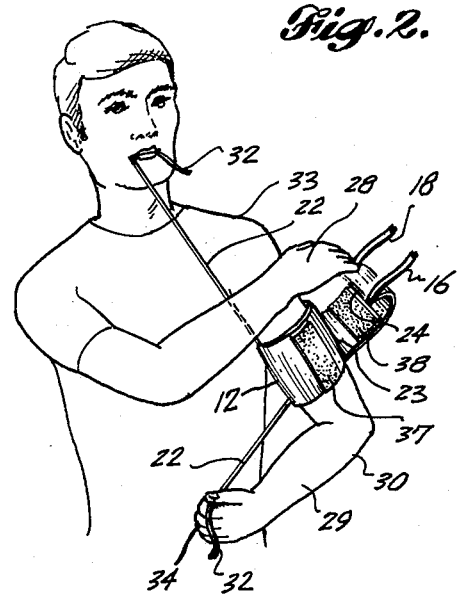
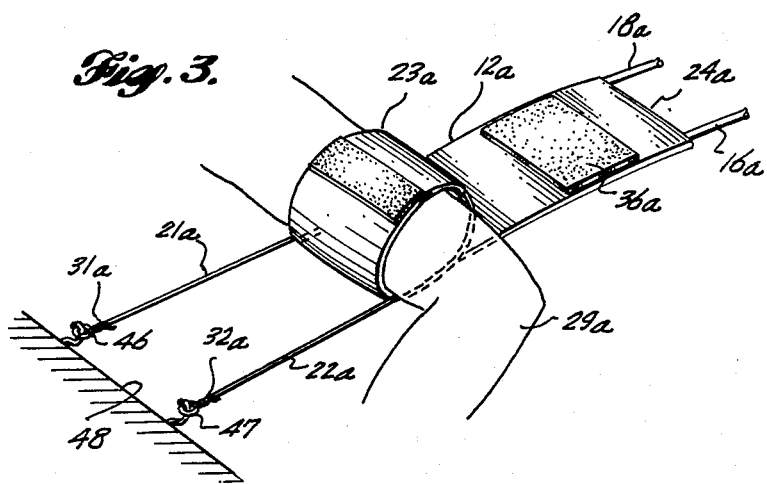
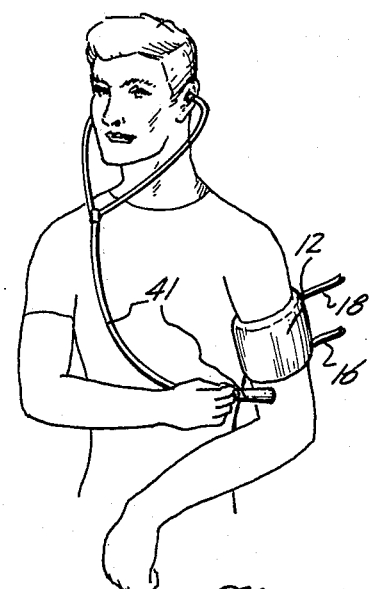
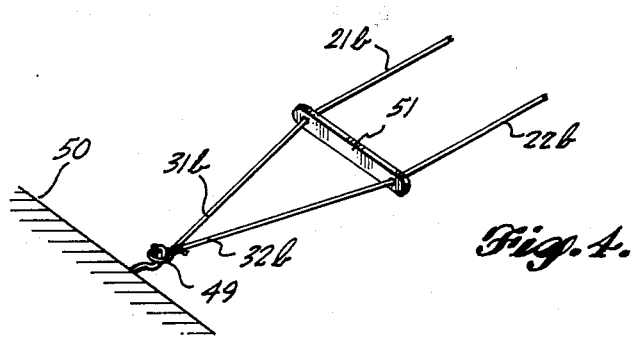

SPHYGOMANOMETER BAND AND METHOD OF SELF-APPLICATION THEREOF

BACKGROUND OF THE INVENTION

The present invention pertains to sphygomanometers for measuring blood pressure in humans.

In general, sphygomanometers include an elongate, pliable, inflatable band which is adaped to be wrapped around and circumferentially tensioned about the upper arm of a patient. A manual air pump is connected to an inflatable bladder carried within the band, and a pressure gage is similarly connected to the bladder to measure the air pressure therewithin at any instant. Typically the band is provided with fastening means so that it may be secured in place about the patient's arm under a predetermined initial tension. By thereafter inflating the band bladder, circumferential pressure on the patient's arm is increased to a measured level which impedes the flow of blood through the arteries of the arm at the location of the sphygomanometer band.

By varying the amount of air pressure applied to the bladder of the band, and simultaneously listening to the sound of the blood as it is pumped by the heart through the arteries of the arm by a stethoscope, it is possible to measure the systolic and diastolic blood pressures of the patient. The systolic pressure corresponds to the arterial blood pressure at which blood is just barely being pumped through the artery, at the point of constriction caused by the inflated arm band. This pressure level is identified by a unique "tapping" sound made by the blood as it is pumped through the restricted artery, with the corresponding blood pressure being read from the pressure gage associated with the inflatable sphygomanometer band at the instant "tapping" sound occurs. The systolic blood pressure corresponds to the relatively higher blood pressure measurement. The lower, diastolic pressure, is ascertained by releasing air from the inflated band to decrease the amount of constriction applied to the patient's arm, and monitoring the blood flow sounds by the stethoscope, noting the pressure at which "tapping" sounds become muffled. The pressure at this point corresponds to the diastolic blood pressure.

The levels of these blood pressures are important in monitoring the physical condition of the patient, and more particularly diagnosing dangerously high or low blood pressure levels. The present invention is particularly concerned with the ability of the patient to measure his own blood pressure, without the assistance of medical personnel or other attendants. It is now generally recognized that blood pressure, and more particularly extremes thereof, are significant contributing factors to heart disease. Moreover, it is believed that transitory periods of high blood pressure in a patient can be controlled or lowered by the conscious action of the patient himself, if he is aware of a temporary high blood pressure condition. Typically, medicine can be taken, or the patient can consciously relax, take a rest or otherwise ameliorate the activity which has induced the high blood pressure.

This ability of the patient to control his own activity in response to temporary blood pressure conditions, has resulted in the recommendation by doctors and other medical authorities, that the patient be equipped with his own sphygomanometer and stethoscope in order to monitor his blood pressure at home or at work, without requiring frequent trips to the doctor's office or hospital. This allows a more effective use of relaxation techniques for reducing temporary excesses of blood pressure.

SUMMARY OF THE PREFERRED EMBODIMENT OF THE INVENTION AND ITS OBJECTIVES

Accordingly, it is an object of the present invention to provide method and apparatus for facilitating the self-application of a sphygomanometer, whereby a patient can readily monitor his own blood pressure without the assistance of another person.

In general, the present invention provides an improved sphygomanometer having a pair of elongate tensioning cords attached to an end of the elongate, pliable, inflatable sphygomanometer band which permits one end of the band to be positioned on the upper arm of the patient and held in a proper position by the cords, while the free end of the elongate band is wrapped around the arm, and secured in place, under circumferential tension, by the fastening means provided on the band.

Prior to this invention, it was extremely difficult, if not impossible, for some patients to apply the sphygomanometer band to their upper arm without assistance. Because the arm to which the band is applied is temporarily disabled, only one hand is available to manipulate both ends of the sphygomanometer band, thus rendering difficult this otherwise simple task.

The present invention alleviates this difficulty, allowing most all patients, including elderly patients who have lost some of their physical agility, to apply the sphygomanometer band and thus achieve the anticipated benefits of being able to monitor their own blood pressure.

These and further features, objects and advantages of the present invention will become apparent to those skilled in the art from a consideration of the following detailed description and appended drawings of particular, exemplary embodiments thereof.

BRIEF DESCRIPTION OF THE DRAWINGS

FIG. 1 is a perspective view of the improved sphygomanometer according to the present invention, during an initial stage of the procedure for self-application of the inflatable band to the patient's upper arm.

FIG. 2 is another perspective view illustrating a second stage of the procedure by which the tensioning cords attached to the end of the band are secured in a manner which frees the opposite arm of the patient for grasping and tightening the free end of the inflatable sphygomanometer band.

FIG. 3 is a perspective view illustrating an alternative method of applying the band in which the tensioning cords are attached to a stationary anchoring point.

FIG. 4 is a further alternative embodiment in which the ends of the tensioning cords are joined at a common anchoring point, with a rigid separator maintaining a suitable separation between the cords.

FIG. 5 is a perspective view of the blood pressure measurement by the patient using a stethoscope after the inflatable band has been properly applied.

DESCRIPTION

With reference to FIGS. 1 and 2, the illustrated embodiment of the present invention provides an improved sphygomanometer 11 including the elongate, pliable, inflatable band 12, for facilitating the self application of the band to the upper arm of the patient without the assistance of another person. The band 12, known per se, is usually formed of a cloth covered elongate inflatable bladder adapted to be wrapped about the upper arm of the patient and pressurized to constrict the arterial flow of blood within the upper arm at the point of application. An elastomeric hand pump 13 having a manually controlled relief valve 14 is connected to the inflatable bladder of band 12 by a flexible air hose or tubular conduit 16. A pressure gauge 17 is similarly connected to the inflatable bladder of band 12 by a hose or tubular conduit 18 to register the instantaneous air pressure within the bladder, whereby the bladder or band pressure may be correlated to the amount of circumferential constriction applied to the arm. Thus, by using the pressure measurement registered by gauge 17 in conjunction with a stethoscope as illustrated in FIG. 5, it is possible to take reliable blood pressure measurements or readings in the manner described hereinabove.

As indicated however, patients have encountered difficulty in positioning and wrapping band 12 in place on their upper arm, due to the partial disablement of the arm to which the band is applied, leaving only one free hand and arm to carry out the necessary manipulations. To alleviate this difficulty, the present invention provides an improved sphygomanometer band 12 to which a pair of elongate tensioning strings or cords 21 and 22 are attached to permit the patient as shown in FIGS. 1 and 2 to hold one end 23 of band 12 in place and under tension while the remaining end 24 of the band is drawn taut in a circumferential wrap around the arm. More particularly, cords 21 and 22 may be provided by any suitable elongated, yieldable material capable of being grasped and held taut by the patient, and may be sewn into the cloth fabric typically provided for covering the inflatable bladder of band 12.

One end of each of cords 21 and 22 is preferably fastened to band end 23 adjacent the opposed longitudinal edge portions 26 and 27 of the band in order to establish a spacing between the cords for accommodating the width of band 12 when it is passed between the cords and wrapped around the remaining circumference of the arm. The length of the cords is not critical, however, they may extend from end 23 of the band by a length of approximately 1-½ to 3 feet.

In one method of using the improved sphygomanometer band 12, an interior surface 38 of the band adjacent end 23 is placed on the upper portion of the patient's arm as shown in FIG. 1 with the length of band 12 depending downwardly on the inside of the arm and with cords 21 and 22 being draped downwardly on the opposite and the laterally outward side of the arm. To facilitate this initial application, the arm may be held in a generally outwardly horizontally extended posture.

The free hand 28 of the patient's opposite arm now releases end 23 of the band and immediately grasps cords 21 and 22 from beneath arm 29 to which the band is applied. The cords are now tensioned slightly and allowed to slip in hand 28 as it is pulled away from arm 29 laterally across the front of the patient's body, thus maintaining end 23 of band 12 in place on arm 29 throughout this sequence of operations. While continuing to apply a slight tension to cords 21 and 22 sufficient to hold end 23 with band 12 in place as shown in FIG. 1, hand 28 manipulates ends 31 and 32 of cords 21 and 22 into a position whereby cord 22 located adjacent band edge 27 and thus next to elbow 30 of arm 29, may be grasped at end 32 by hand 34 of arm 29 as shown in FIG. 2. For this purpose, the lower arm portion of arm 29 may be bent at elbow 30 to extend at a right angle to the upper arm to position hand 34 for holding end 32 of cord 22 under tension at a point substantially front and center of the patient's body. This configuration is best shown in FIG. 2.

After anchoring cord 22 at end 32 by hand 34, the other cord 21 located on band edge 26 adjacent the patient's shoulder 33 is manipulated by hand 28 upwardly to the patient's mouth in which end 32 is grasped between his teeth holding cord 21 and the end of band 12 in place. End 23 of the band 12 is now held by the tension forces in cords 21 and 22 which extend circumferentially outwardly, around and under the upper portion of arm 29 such that the patient's free hand 28 may now be extended over arm 29 to grasp the free end 24 of band 12 and pull it upwardly and around arm 29 under a tension circumferentially opposed to the tension previously established in cords 21 and 22. During this operation, air hoses 16 and 18 may be disconnected either from band 12 or from hand pump 13 and gauge 17, respectively, in order to free the band end 24 for being wrapped around the arm. After the band is brought upwardly and around arm 29 in circumferentially overlapping position with respect to end 23, the entire band may be secured in place by conventional fastening means, such as complementary male and female snap fasteners or, as in the present embodiment, by complementary synthetic fibrous loop and hook fabrics 36 and 37 provided on the interior surface 38 and exterior surface 39, respectively, of band 12 adjacent the opposed ends 23 and 24 thereof. After band 12 has been secured to a taut or circumferentially tensioned condition by the fastening means, then cords 21 and 22 may be released and the patient may proceed with a blood pressure measurement utilizing a stethoscope 41 as shown in FIG. 5.

An alternative embodiment of the improved sphygomanometer band and method is illustrated in FIG. 3, in which the tensioning cords 21a and 22a are provided with releasable fasteners 46 and 47 at ends 31a and 32a for detachable connection to a stationary anchor point 48 located laterally of arm 29a toward the patient's opposite arm. This anchor point 48 may be provided by a wall, desk, doorway, etc., in the patient's home or office. In this instance, fasteners 46 and 47 may be provided by simple hook and ring members as illustrated.

The method of applying band 12a is similar to the technique described above, except that after band end 23a is positioned on the upper portion of arm 29a, the patient attaches releasable fasteners 46 and 47 to anchor point 48, and applies tension to cords 21a and 22a by manipulating arm 29a and simultaneously pulling end 24a of band 12a taut in circumferential opposition to the tension in the cords during the wrapping operation.

In FIG. 4, a still further alternative embodiment of the improved sphygomanometer band and method is illustrated in which tensioning cords 21b and 22b are provided with a single releasable fastener 49 to which both ends 31b and 32b are attached for releasable connection to an anchor point 50. A spreader bar 51 provided at a position proximate ends 31b and 32b of the cords serves to maintain a suitable separation between tensioning cords 21b and 22b adjacent the arm to which the band is applied in order to permit the end of the band corresponding to end 24a of FIG. 3 to be threaded or passed through the separated cords 21b and 22b during the wrapping operation.

It is observed in connection with the embodiments of FIGs. 3 and 4, that the anchor points 48 and 50 may alternatively be disposed laterally to the outside of arm 29a and thus to the side of the patient's body adjacent the arm to which the band is applied, such that the tensioning cords extend directly outwardly from band end 23a generally tangent to the upper portion of arm 29a, i.e., without extending circumferentially downwardly and under the arm as in the embodiments shown by the drawings.

While only a limited number of embodiments of the present invention have been disclosed herein, it will be readily apparent to persons skilled in the art that numerous changes and modifications may be made thereto without departing from the spirit of the invention. Accordingly, the foregoing disclosure and description thereof are for illustrative purposes only and do not in any way limit the invention which is defined only by the following claims.

I claim:
1. An improved sphygomanometer having an elongate, pliable, inflatable band capable of being self-applied by the patient to an upper portion of one of his arms wherein the improvement comprises:
 a pair of elongate tensioning cords each having one end connected to a first end of said inflatable band adjacent opposite longitudinal edge portions thereof, whereby the patient may dispose the first end of said band on his arm and hold it in place by applying tension to said cords while a second end of said band is pulled taut and wrapped circumferentially about the arm overlapping said first band end.

2. In a sphygomanometer having an elongate, pliable, inflatable band adapted to be wrapped circumferentially around the upper portion of one arm of the patient and secured thereon under a circumferential tension and having a manually operated air pump means and an air pressure measuring means connected to said inflatable band, the combination therewith comprising:
 a pair of elongate tensioning cords each having one end fastened to a first end of said band adjacent opposed longitudinal edge portions thereof for facilitating self-wrapping of said band by the patient, whereby said first end of said band may be held in place on the patient's arm by applying tension to said cords at points spaced from their fastened ends while at the same time pulling a second end of said band taut and wrapping it between said cords around the arm overlapping said first band end and securing said band to itself under circumferential tension.

3. The improved sphygomanometer of claim 1 further comprising:
 detachable fastening means mounted to said tensioning cords at locations thereon longitudinally spaced from said first end of said inflatable band, said fastening means being adapted for detachable connection to a stationary anchor point adjacent the patient's arm for applying tension to said cords while the second end of said band is pulled taut and wrapped around the patient's arm.

4. The improved sphygomanometer of claim 1, wherein the improvement further comprises:
 releasable fastening means jointly connected to said tension cords at a longitudinal position thereon spaced apart from said first end of said inflatable band and being adapted for releasable attachement to a stationary anchor point adjacent the patient's upper arm for applying said tension to said cords while a second end of said band is pulled taught and wrapped around the patient's arm; and
 spreader bar means mounted between said tensioning cords intermediate said first end of said inflatable band and said releasable fastening means for maintaining separation between said cords adjacent said first end of said inflatable band, whereby said second band end may be passed between said cords as said band is wrapped around the patient's arm.

5. A method by which a patient applies an elongated sphygomanometer band to an upper portion of one of his arms, comprising the steps of:
 fastening a pair of tensioning cords to a first end of said band adjacent opposed longitudinal edge portions thereof;
 placing said first end of said band on said upper arm with a second end of said band and said cords extending generally about said arm in opposite circumferential directions;
 applying tension to said cords at locations thereon spaced apart from said arm and from said first end of said band so that said cords become taut and extend substantially tangentially to the arm in spaced apart parallelism with the spacing between said cords substantially corresponding to the width of said band; and
 grasping a second end of said band and pulling it taut against the tension established in said cords at the first end of said band and circumferentially wrapping said second end of said band about the arm passing it between said tensioned cords and securing said band in a tension condition on said arm.

6. The method set forth in claim 5, wherein said steps are further defined by:
 placing said first end of said band on the upper portion of said first named arm with said cords extending downwardly adjacent the outside of such arm and the second end of said band extending downwardly adjacent the inside of said first named arm;
 passing said cords underneath said first named arm and to either side of said downwardly extending second band end and grasping said cords with the hand of the patient's second arm, allowing the cords to slip under tension in said hand while drawing said hand generally toward the front center of the patient's body;
 grasping one of said cords with the hand of said first named arm and grasping the other said cord in the patient's mouth to free the hand of the second arm;
 reaching with the hand of the second arm over the upper portion of the first named arm and grasping the second end of said band and pulling it upwardly adjacent the outside of said first named arm and circumferentially wrapping said band about such arm overlapping the first end of said band therewith; and
 securing said band in said circumferentially wrapped and tensioned condition with said hand of said second arm.

* * * * *